(12) United States Patent
Bernard et al.

(10) Patent No.: US 8,940,680 B2
(45) Date of Patent: Jan. 27, 2015

(54) COMPOSITION CONTAINING SUPERABSORBENT POLYMERS

(75) Inventors: Anne-Laure Bernard, Neuilly / Seine (FR); Odile Aubrun-Sonneville, Antony (FR); Laurence Leroy, St Remy les Chevreuses (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/705,121

(22) Filed: Feb. 12, 2010

(65) Prior Publication Data

US 2010/0139704 A1 Jun. 10, 2010

Related U.S. Application Data

(63) Continuation of application No. 11/865,860, filed on Oct. 2, 2007, now abandoned.

(60) Provisional application No. 60/850,630, filed on Oct. 11, 2006.

(30) Foreign Application Priority Data

Oct. 4, 2006 (FR) .................................... 06 54074

(51) Int. Cl.
| | | |
|---|---|---|
| *C11D 3/37* | (2006.01) | |
| *C11D 1/90* | (2006.01) | |
| *C11D 3/22* | (2006.01) | |
| *A61K 8/40* | (2006.01) | |
| *A61K 8/72* | (2006.01) | |
| *A61K 8/73* | (2006.01) | |
| *A61Q 1/14* | (2006.01) | |
| *A61K 8/04* | (2006.01) | |
| *A61K 8/44* | (2006.01) | |
| *A61K 8/60* | (2006.01) | |
| *A61K 8/81* | (2006.01) | |
| *A61Q 19/10* | (2006.01) | |

(52) U.S. Cl.
CPC . *A61K 8/042* (2013.01); *A61K 8/44* (2013.01); *A61K 8/60* (2013.01); *A61K 8/604* (2013.01); *A61K 8/73* (2013.01); *A61K 8/731* (2013.01); *A61K 8/732* (2013.01); *A61K 8/8147* (2013.01); *A61K 8/8152* (2013.01); *A61K 8/8158* (2013.01); *A61Q 1/14* (2013.01); *A61Q 19/10* (2013.01); *A61K 2800/54* (2013.01)
USPC ........... 510/475; 510/121; 510/123; 510/151; 510/155; 510/158; 510/403; 510/470; 510/476; 424/401; 424/70.13; 424/70.16; 424/70.19; 424/70.21; 424/70.31

(58) Field of Classification Search
CPC .............. C11D 1/90; C11D 3/22; C11D 3/37; C11D 3/3757; C11D 1/662; A61K 8/40; A61K 8/604; A61K 8/72; A61K 8/73; A61Q 1/14
USPC ......... 510/121, 123, 151, 155, 158, 403, 470, 510/475, 476; 424/401, 70.13, 70.16, 424/70.19, 70.21, 70.31
See application file for complete search history.

(56) References Cited

U.S. PATENT DOCUMENTS

| | | | |
|---|---|---|---|
| 5,703,026 A | | 12/1997 | Setser et al. |
| 5,965,502 A | * | 10/1999 | Balzer ........................... 510/158 |
| 2003/0035783 A1 | * | 2/2003 | Birkel et al. .................. 424/70.2 |
| 2004/0097385 A1 | * | 5/2004 | Chen et al. ..................... 510/130 |
| 2005/0238680 A1 | * | 10/2005 | Stella et al. ................... 424/401 |

FOREIGN PATENT DOCUMENTS

| | | |
|---|---|---|
| EP | 1 195 157 | 4/2002 |
| FR | 2 805 461 | 8/2001 |

* cited by examiner

*Primary Examiner* — Brian P Mruk
(74) *Attorney, Agent, or Firm* — Oblon, Spivak, McClelland, Maier & Neustadt, L.L.P.

(57) ABSTRACT

Composition in the form of a gel containing at least 35% by weight of water, at least one foaming surfactant chosen from nonionic or amphoteric surfactants, and at least one superabsorbent polymer. The superabsorbent polymer helps to thicken the composition without affecting its cosmetic properties.

13 Claims, No Drawings

COMPOSITION CONTAINING SUPERABSORBENT POLYMERS

REFERENCE TO PRIOR APPLICATIONS

This application is a continuation application of U.S. application Ser. No. 11/865,860, filed on Oct. 2, 2007, which claims priority to U.S. provisional application 60/850,630 filed Oct. 11, 2006, and to French patent application 0654074 filed Oct. 4, 2006, both incorporated herein by reference.

FIELD OF THE INVENTION

The invention relates to a cleansing composition, preferably in the form of a gel, comprising a superabsorbent polymer, and to uses thereof in, e.g., the cosmetics or dermatological fields, in particular as a cleansing or makeup-removing product for the skin, the hair, including the scalp, and/or the mucous membranes (lips).

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Cleansing the skin is very important for facecare, and it should be as effective as possible since fatty residues such as excess sebum, residues of cosmetic products used daily and makeup products, in particular waterproof products, accumulate in the folds of the skin and can block the pores of the skin and lead to the appearance of spots.

The foaming cleansing products currently marketed are in the form of foaming bars, gels or creams, and they may or may not contain soaps. Some consumers complain that foaming products containing soaps cause tautness due to them being too detergent. It is therefore often preferable to prepare foaming products without soaps so as to have better tolerance. The cleansing products not containing soaps which are currently on the market generally have a low viscosity and, as a result, are not always practical to use because they have a tendency to run.

In order to thicken soap-free foaming products it is known practice to add, to the latter, thickeners such as oxyethylenated compounds, polymers, for instance cellulose gums or derivatives thereof, guar gums or derivatives thereof, acrylic polymers, including those possibly containing a hydrophobic portion and therefore having an amphiphilic character. Thus, document EP-A-1,172,095 describes a foaming composition containing silica and an oxyethylenated compound such as, for example, PEG-120 methyl glucose dioleate.

However, when the percentage of these thickening compounds is increased so as to have a thicker composition, this brings about drawbacks. Thus, when the percentage of oxyethylenated compounds is increased, the spreading over the skin occurs in packets and is not homogeneous. When the percentage of acrylic polymer is increased, the products obtained can be viscous, but result in a mediocre beginning of lathering. Moreover, the addition of too high percentage of gum causes the start of lathering to be impaired and affects the qualities of the foam.

It is therefore difficult to thicken foaming media while at the same time conserving the required properties, i.e. good mixing with water and a rapid conversion to foam, and homogeneous spreading when applied to the skin.

SUMMARY OF THE INVENTION

There remains therefore a need for thick foaming compositions with a very good foam and spreading quality.

The inventors have discovered, surprisingly, that it is possible to achieve obtain a foaming product with good cosmetic properties (e.g., foam qualities, quality of spreading on the skin) while at the same time being sufficiently thick, by using a superabsorbent polymer in the form of particles, in a composition containing nonionic and/or amphoteric foaming surfactants. These polymers are in the form of particles which swell greatly in water and generate viscosity by compact stacking, even in a surfactant medium. During application, the surfactants are readily released due to the effect of the shear and they generate foam.

While U.S. Pat. No. 5,703,026 describes cleansing compositions containing a superabsorbent polymer, these compositions are solids (bars), and not gels which are flexible compositions. Thus, the compositions described in said document have a structure that is entirely different from that of the compositions of the present invention, which contain more water and have good foaming properties while at the same time having a satisfactory viscosity to give a gel.

DETAILED DESCRIPTION OF THE PREFERRED EMBODIMENTS

Thus, a subject of the present invention is a cleansing composition for topical application, in the form of a gel and containing, in a physiologically acceptable aqueous medium, at least 35% by weight of water relative to the total weight of the composition, at least one foaming surfactant chosen from nonionic surfactants and amphoteric surfactants, and at least one superabsorbent polymer.

The superabsorbent polymer is in the form of particles.

The term "topical application" is herein intended to mean an external application to keratin materials, namely, in particular, the skin, the scalp, the eyelashes, the eyebrows, the nails, the hair and/or the mucous membranes. Since the composition is for topical application, it comprises a physiologically acceptable medium. The term "physiologically acceptable medium" is intended to mean a medium compatible with the skin, the lips, the scalp, the eyelashes, the eyes, the nails and/or the hair. The composition can in particular constitute a cosmetic or dermatological composition.

The term "gel" is intended to mean a gelled composition, which is flexible, as opposed to a solid product, and the viscosity of which can be measured.

Moreover, the term "aqueous medium" is intended to mean a medium containing an amount of water of at least 35% by weight, preferably of at least 40% by weight, better still of at least 50% by weight, and even better still of at least 60% by weight, relative to the total weight of the composition. This amount can range, for example, from 35% to 98% by weight, preferably from 40% to 98% by weight, better still from 50% to 80% by weight, and even better still from 60% to 80% by weight, relative to the total weight of the composition.

The aqueous medium of the foaming compositions of the invention can optionally contain, in addition to the water, further ingredients such as one or more solvents chosen from lower alcohols containing from 1 to 6 carbon atoms, such as ethanol; polyols such as glycerol; glycols such as butylene glycol, isoprene glycol, propylene glycol or polyethylene glycols, such as PEG-8; sorbitol; sugars such as glucose, fructose, maltose, lactose or sucrose; and mixtures thereof. The amount of solvent(s) in the composition of the invention can range from 0.5% to 30% by weight, and preferably from 5% to 20% by weight, relative to the total weight of the composition.

The term "foaming surfactant" is intended to mean a surfactant which has foaming properties when it is introduced into water. The foaming surfactants are detergents and differ from emulsifying surfactants by virtue of the value of their HLB (Hydrophilic Lipophilic Balance), which is generally greater than 15 and better still greater than 18 or even than 20, the HLB being the ratio of the hydrophilic part to the lipophilic part in the molecule. The term "HLB" is well known to those skilled in the art and is described, for example, in "The HLB system. A time-saving guide to Emulsifier Selection" (published by ICI Americas Inc; 1984).

The compositions of the invention are preferably foaming cleansing compositions which can be used in the field of cleansing the skin, the hair or the mucous membranes. They are generally rinse-off compositions.

The composition obtained is preferably in the form of a gel, and the viscosity of the compositions according to the invention preferably range from 0.1 to 50 Pa·s, measured at 25° C. using a rheomat RM180 from Rheometric Scientific at 200 rpm (revolutions per minute), 10 minutes after the rotor has begun to rotate. The device is equipped with a different rotor according to the viscosities, for example with a rotor 2 for viscosity ranges less than 0.7 Pa·s, with a rotor 3 for viscosity ranges of 0.2 to 4 Pa·s, and with a rotor 4 for viscosity ranges greater than 2 Pa·s.

While not bound by any theory, it is believed that the superabsorbent polymers contribute to the composition's good cosmetic properties. In addition, it is believed that they help in providing textures with a frosty appearance, i.e. the appearance of frosted glass, which are very original and produce a fondant gentle scrub effect when applied.

Superabsorbent Polymers

The term "superabsorbent polymer" is intended to mean a polymer which swells in water, in particular a cross-linked polymer. The superabsorbent polymer used in the composition of the invention is in the form of particles, which, once hydrated, swell, forming soft beads which preferably have a number-average diameter of from 10 μm to 1000 μm. In order to better achieve the full aim of the invention and to provide good thickening of the compositions, the superabsorbent polymers are preferably in the form of particles.

The superabsorbent polymers can in particular be chosen from:
  crosslinked sodium polyacrylates such as, for example, those sold under the names Octacare X100, X110 and RM100 by the company Avecia, those sold under the names Flocare GB300 and Flosorb 500 by the company SNF, those sold under the names Luquasorb 1280 and Luquasorb 1110 by the company BASF, and those sold under the names Water Lock G400 and G430 (INCI name: acrylamide/sodium acrylate copolymer) by the company Grain Processing,
  starches grafted with an acrylic polymer (homopolymer or copolymer) and in particular with sodium polyacrylate, such as those sold under the names Sanfresh ST-100C, ST100MC, IM-300MC by the company Sanyo Chemical Industries (INCI name: sodium polyacrylate starch),
  hydrolysed starches grafted with an acrylic polymer (homopolymer or copolymer) and in particular acryloacrylamide/sodium acrylate copolymer, such as those sold under the names Water Lock A-240, A-180, B-204, D-223, A-100, C-200, D-223, by the company Grain Processing (INCI name: starch/acrylamide/sodium acrylate copolymer),
  polymers based on starch, on gum and on a cellulose derivative, such as that containing starch, guar gum and sodium carboxymethylcellulose, sold under the name Lysorb 220 by the company Lysac,
  and mixtures thereof.

The amount of superabsorbent polymer(s) in the composition of the invention depends on the surfactants present and on the desired viscosity for the product to be obtained. It can range, for example, from 0.1% to 20% by weight, preferably from 0.5% to 20% by weight, better still from 0.5% to 10% by weight, and even better still from 0.5% to 5% by weight, relative to the total weight of the composition, including all weights and weight ranges between stated values.

Foaming Surfactants

The composition contains at least one foaming surfactant chosen from nonionic surfactants and amphoteric surfactants, i.e. it may contain only one or more nonionic surfactants, or only one or more amphoteric surfactants, or a mixture of one or more nonionic surfactants and of one or more amphoteric surfactants.

The composition can optionally contain one or more anionic surfactants, provided that said surfactants are preferably present in an amount of at most 2% by weight relative to the total weight of the composition. However, the composition is preferably free of anionic surfactants.

Furthermore, the composition can optionally contain one or more cationic surfactants such as, for example, myristyltrimethylammonium bromide, but cationic surfactants are preferably present in an amount of at most 1% by weight relative to the total weight of the composition.

The total amount of foaming surfactants (on an active material basis) can vary according to the final use of the compositions. It can, for example, range from 3% to 20% by weight, and preferably from 3% to 15% by weight, relative to the total weight of the composition. The term "total amount" is intended to mean the amount of all the foaming surfactants, including anionic and cationic surfactants, if they are present.

According to a preferred embodiment, the composition contains at least one nonionic surfactant and at least one amphoteric surfactant. In addition, according to a more preferred embodiment, the amount of nonionic surfactant is greater than the amount of amphoteric surfactant.

Nonionic Surfactants

As nonionic surfactants, use may, for example, be made of alkyl polyglucosides (APGs), maltose esters, polyglycerolated fatty alcohols, glucamine derivatives such as 2-ethylhexyloxycarbonyl-N-methylglucamine, and mixtures thereof.

As alkylpolyglucosides, use is preferably made of those containing an alkyl group containing from 6 to 30 carbon atoms, and preferably from 8 to 16 carbon atoms, and containing a hydrophilic (glucoside) group preferably comprising 1, 2 or 3 saccharide units. As alkylpolyglucosides, mention may, for example, be made of decylglucoside (alkyl-C9/C11-polyglucoside (1.4)) such as the product sold under the name MYDOL 10® by the company Kao Chemicals, the product sold under the name PLANTAREN 2000 UP® by the company Cognis, and the product sold under the name ORAMIX NS 10® by the company Seppic; caprylyl/capryl glucoside such as the product sold under the name ORAMIX CG 110® by the company Seppic; laurylglucoside such as the products sold under the names PLANTAREN 1200 N® and PLANTACARE 1200® by the company Cognis; and cocoglucoside such as the product sold under the name PLANTACARE 818/UP® by the company Cognis.

The maltose derivatives are, for example, those described in document EP-A-566438, such as the O-octanoyl-6'-D-maltose or the O-dodecanoyl-6'-D-maltose described in document FR-2,739,556.

Among the polyglycerolated fatty alcohols, mention may be made of polyglycerolated dodecanediol (3.5 mol of glycerol), a product sold under the name CHIMEXANE NF® by the company Chimex.

According to a preferred embodiment of the invention, the nonionic surfactants are chosen from alkylpolyglucosides.

Amphoteric Surfactants

The amphoteric (or zwitterionic) surfactants can be chosen, for example, from betaine derivatives, alkyl amphoacetates, hydroxysultaines, and mixtures thereof.

As betaine derivatives, mention may, for example, be made of cocobetaine, such as the product sold under the name DEHYTON AB-30® by the company Cognis, laurylbetaine, such as the product sold under the name GENAGEN KB® by the company Clariant, oxyethylenated laurylbetaine (10 OE), such as the product sold under the name LAURYLETHER (10 OE) BETAINE® by the company Shin Nihon Rica, oxyethylenated stearylbetaine (10 OE), such as the product sold under the name STEARYLETHER (10 OE) BETAINE® by the company Shin Nihon Rica, the cocamidopropyl betaine sold, for example, under the name VELVETEX BK 35® by Cognis, or else the undecylene-amidopropyl betaine sold, for example, under the name AMPHORAM U® by Ceca.

As alkylamphoacetates, mention may, for example, be made of N-disodium N-cocoyl-N-carboxymethoxyethyl-N-carboxymethylethylenediamine (INCI name: disodium cocamphodiacetate), such as the product sold under the name MIRANOL C2M CONCENTRE NP® by the company Rhodia Chimie, and N-sodium N-cocoyl-N-hydroxyethyl-N-carboxymethylethylenediamine (INCI name: sodium cocamphoacetate).

As hydroxysultaines, mention may be made of cocamidopropyl hydroxysultaine, such as the product sold under the name REWOTERIC AM CAS by the company Goldschmidt-Degussa.

According to a preferred embodiment of the invention, the amphoteric surfactants are chosen from betaine derivatives.

According to a more preferred embodiment of the invention, the composition contains at least one nonionic surfactant and at least one amphoteric surfactant.

Other Surfactants

As indicated above, the composition of the invention can optionally contain one or more other anionic and/or cationic surfactants. However, according to a preferred embodiment of the invention, the composition is free of anionic surfactant since anionic surfactants affect the thickening of the compositions containing the superabsorbent polymer.

When the composition contains one or more anionic surfactants, the amount of these anionic surfactants (on an active material basis) should preferably be at most 2% by weight, preferably at most 1.5% by weight, and even better still preferably at most 1.2% by weight, relative to the total weight of the composition. This amount can preferably range from 0 to 2% of the total weight of the composition.

When the composition contains one or more cationic surfactants, the amount of these cationic surfactants (on an active material basis) should preferably be at most 1% by weight, better still preferably at most 0.5% by weight, relative to the total weight of the composition. This amount can preferably range from 0 to 1% of the total weight of the composition.

Additives

The composition of the invention can contain further additives and/or active agents. Mention may, for example, be made of preserving agents, in particular cationic preserving agents such as biguanide; sequestering agents (EDTA); antioxidants; fragrances; dyestuffs such as soluble dyes, pigments or pearlescent agents; mineral or organic fillers, which provide viscosity, matting agents, bleaching agents or exfoliants; sunscreens; hydrophilic or lipophilic active cosmetic or dermatological agents, such as water-soluble or liposoluble vitamins, antiseptics, antiseborrhoeic agents, antimicrobials such as benzoyl peroxide, salicylic acid, triclosan, azelaic acid, niacinamide (vitamin PP), and also optical brighteners; nonionic, anionic, cationic and/or amphoteric polymers; fatty substances incompatible with the aqueous medium, such as oils or waxes; viscosity modifiers and thickeners; exfoliants; oil or fatty substance dispersions; or other agents having the effect of improving the cosmetic properties of hair or of the skin. The amounts of these various adjuvants are those conventionally used in the field under consideration, and are, for example, from 0.01% to 20% of the total weight of the composition. These adjuvants and the concentrations thereof should be such that they do not modify the property desired for the composition of the invention and that they do not destabilize it.

As fillers, mention may in particular be made of silica, starch or nylon.

As exfoliants, mention may, for example, be made of exfoliant or scrubbing particles of mineral, plant or organic origin. Thus, use may, for example, be made of polyethylene beads or powder, nylon powder, polyvinyl chloride powder, pumice, ground apricot kernel or walnut husk, sawdust, glass beads and alumina, and mixtures thereof. These particles can be present in an amount ranging, for example, from 0.5% to 40% by weight, preferably from 1% to 20% by weight, and better still from 1% to 10% by weight, relative to the total weight of the composition. When the composition contains exfoliant particles, it can in particular constitute a scrubbing composition for facial or body skin.

According to a preferred embodiment of the invention, the composition contains at least one cationic polymer.

As cationic polymers that can be used in the composition of the invention, mention may, for example, be made of polymers comprising at least one quaternary amine group and, optionally, primary, secondary, tertiary and/or quaternary amine groups which are part of the polymer chain or directly connected thereto. These polymers generally have a molecular weight ranging from 500 to approximately 5 000 000, and preferably from 1000 to 3 000 000.

Among these polymers, mention may more particularly be made of the following cationic polymers:

(1) Homopolymers or copolymers derived from acrylic or methacrylic esters or amides and comprising at least one quaternary ammonium group, and in particular one of the units of formulae below:

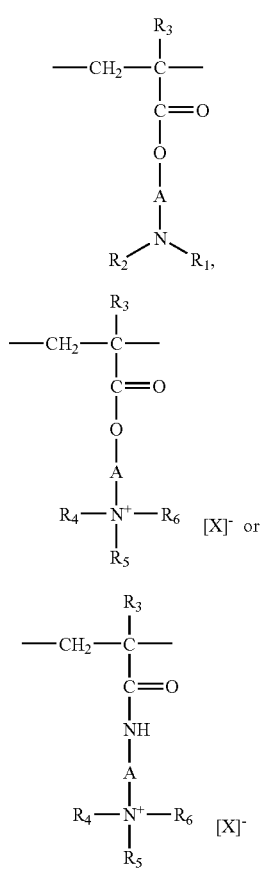

in which:

$R_3$ denotes a hydrogen atom or a $CH_3$ radical;

A is a linear or branched alkyl group of 1 to 6 carbon atoms or a hydroxyalkyl group containing from 1 to 4 carbon atoms;

$R_4$, $R_5$ and $R_6$, which may be identical or different, represent an alkyl group containing from 1 to 18 carbon atoms or a benzyl radical;

$R_1$ and $R_2$ represent a hydrogen atom or an alkyl group containing from 1 to 6 carbon atoms;

X denotes a methosulphate anion or a halide such as chloride or bromide.

The copolymers of family (1) also contain one or more units derived from comonomers which may be chosen from the family of acrylamides, methacrylamides, diacetone acrylamides, acrylamides and methacrylamides substituted on the nitrogen with lower alcohols, acrylic or methacrylic acids or esters thereof, vinyllactams such as vinylpyrrolidone or vinylcaprolactam, and vinyl esters.

Thus, among these copolymers of family (1), mention may, for example, be made of:

copolymers of acrylamide and of dimethylaminoethyl methacrylate quaternized with dimethyl sulphate or with a dimethyl halide, such as the product sold under the name HERCOFLOC by the company HERCULES;

copolymers of acrylamide and of methacryloyloxyethyltrimethylammonium chloride, such as POLYQUATERNIUM 5 (INCI name) and, for example, the product sold under the name MERQUAT 5 by the company NALCO; and such as POLYQUATERNIUM 15 (INCI name) and, for example, the product sold under the name ROHAGIT KF 720 F by the company ROHM;

the copolymer of acrylamide and of methacryloyloxyethyltrimethylammonium methosulphate sold under the name RETEN by the company HERCULES;

quaternized or non-quaternized vinylpyrrolidone/dialkylaminoalkyl acrylate or methacrylate copolymers, such as POLYQUATERNIUM 11 (INCI name) and, for example, the products sold under the names GAFQUAT 755, GAFQUAT 755N and GAFQUAT 734 by the company ISP;

dimethylaminoethyl methacrylate/vinylcaprolactam/vinylpyrrolidone terpolymers, such as the product sold under the name GAFFIX VC 713 by the company ISP;

the quaternized vinylpyrrolidone/dimethylaminopropyl methacrylamide copolymer such as POLYQUATERNIUM 28 (INCI name) and, for example, the product sold under the name GAFQUAT HS-100 by the company ISP;

copolymers based on vinylpyrrolidone and vinylcaprolactam, such as POLYQUATERNIUM 46 (INCI name) and, for example, the product sold under the name LUVIQUAT HOLD by the company BASF;

terpolymers of acrylic acid and of (meth)acrylamido-trimethylammonium chloride, such as the acrylic acid/methacrylamidopropyltrimethylammonium chloride/methyl acrylate terpolymer sold by the company Nalco under the name Merquat 2001 (INCI name: Polyquaternium 47).

(2) Homopolymers or copolymers of dimethyldiallylammonium of formula (2) described below:

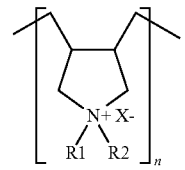

in which:

R1 and R2, which may be identical or different, denote a hydrogen atom or represent an alkyl group containing from 1 to 18 carbon atoms;

X denotes a methosulphate anion or a halide such as chloride or bromide.

The copolymers of family (2) also contain one or more units derived from comonomers which may be chosen from the family of acrylamides, methacrylamides, diacetone acrylamides, acrylamides and methacrylamides substituted on the nitrogen with lower ($C_1$-$C_6$) alkyl radicals, acrylic or methacrylic acids or esters thereof, vinyllactams such as vinylpyrrolidone or vinylcaprolactam, and vinyl esters.

As polymers of family (2), mention may, for example, be made of the following polymers:

dimethyldiallylammonium chloride polymers, such as POLYQUATERNIUM 6 (INCI name) and, for example, the products sold under the names SALCARE SC 30 by the company CIBA, and MERQUAT 100 by the company NALCO;

copolymers of acrylamide and of dimethyldiallylammonium chloride, such as POLYQUATERNIUM 7 (INCI name) and, for example, the products sold under the names MERQUAT S, MERQUAT 2200 and MERQUAT 550 by the company NALCO, SALCARE SC 10 by the company CIBA.

(3) Quaternized polysaccharides such as guar gums containing trialkylammonium cationic groups, for instance the products sold in particular under the trade names JAGUAR C13S, JAGUAR C 15, JAGUAR C 17, JAGUAR C 162, JAGUAR C 2000 and JAGUAR EXCEL by the company MEYHALL; or such as quaternized cellulose derivatives, for instance the hydroxyethylcellulose polymer containing triallylammonium cationic groups, for instance POLYQUATERNIUM 10 (INCI name) and, for example, the product sold under the name UCARE POLYMER JR-400 by the company AMERCHOL.

(4) Quaternary copolymers of vinylpyrrolidone and of vinylimidazole; such as POLYQUATERNIUM 16 (INCI name) and, for example, the products sold under the names LUVIQUAT FC905, LUVIQUAT FC370, LUVIQUAT HM552 and LUVIQUAT FC550 by the company BASF, and POLYQUATERNIUM 44 (INCI name) and, for example, the product sold under the name LUVIQUAT CARE by the company BASF.

(5) Chitosans or salts thereof, such as chitosan acetate, chitosan lactate, chitosan glutamate, chitosan gluconate or chitosan pyrrolidone carboxylate. Among these compounds, mention may be made of the chitosan which has a degree of deacetylation of 90.5% by weight, sold under the name Kytan Brut Standard by the company ABER TECHNOLOGIES, and the chitosan pyrrolidone carboxylate sold under the name KYTAMER PC by the company AMERCHOL.

(6) Cationic cellulose derivatives such as copolymers of cellulose or of cellulose derivatives grafted with a water-soluble monomer comprising a quaternary ammonium, and as described in particular in U.S. Pat. No. 4,131,576, such as hydroxyalkylcelluloses, for instance hydroxymethyl-, hydroxyethyl- or hydroxypropylcelluloses grafted in particular with a methacryloyloxyethyltrimethylammonium salt, methacrylamidopropyltrimethylammonium salt or dimethyldiallylammonium salt. The marketed products corresponding to this definition are more particularly the products sold under the name "CELQUAT L 200" and "CELQUAT H 100" by the company National Starch; and mixtures of these cationic polymers.

The polymers which are particularly preferred are polyquaternium 5, polyquaternium 7, polyquaternium 28, polyquaternium 39, polyquaternium 44 and polyquaternium 47, and mixtures thereof. Polyquaternium 7 is most particularly preferred.

The amount of cationic polymer (on an active material basis) should preferably be such that it does not affect the properties of the composition and in particular that it does not lead to instability. This amount can range, for example, from 0.1% to 1% by weight, and preferably from 0.2% to 0.5% by weight, relative to the total weight of the composition.

According to a specific embodiment of the invention, when the composition of the invention contains a preserving agent, it is preferably a cationic preserving agent. Cationic preserving agents have the advantage, in addition to their protective property against bacteria, of improving the stability of the gel. As cationic preserving agents, mention may, for example, be made of polyhexamethylene biguanide hydrochloride (INCI name: polyaminopropyl biguanide); alkyl-trimethylammonium bromides, the alkyl radical containing from 1 to 22 carbon atoms, and more particularly from 8 to 20 carbon atoms, for instance dodecyltrimethylammonium bromide, hexadecyltrimethylammonium bromide or myristyltrimethylammonium bromide (INCI name: mytrimonium bromide), which can be in a mixture with other ammonium bromides, for example in the mixture of dodecyltrimethylammonium bromide, myristyltrimethylammonium bromide and hexadecyltrimethylammonium bromide sold under the name Cetrimide by the company FEF CHEMICALS.

The preserving agents are present in the composition of the invention in a sufficient amount to act as a preserving agent in the composition. Thus, they may be present in an amount ranging, for example, from 0.001% to 1% of the total weight of the composition, preferably from 0.01% to 1% of the total weight of the composition, and better still from 0.05% to 0.5% of the total weight of the composition.

The compositions according to the invention can have an appearance ranging from the fluid product to a gel. They are stable and have a very good rinsability. They can, for example, constitute a cleansing and/or makeup-removing product for the skin, including the scalp, and/or the hair, a scrubbing product and/or an exfoliant product for the skin (desquamation, peeling). They can more particularly constitute a skin cleansing composition.

A subject of the invention is also the cosmetic use of the composition as defined above, for cleansing and/or removing makeup from the skin and/or the hair, and/or for scrubbing the skin.

The compositions according to the invention can in particular find applications for:

deep cleansing the treatment of greasy skin and/or problem skin cleansing very fragile skin mechanical peelings The compositions according to the invention can in particular constitute a composition for the treatment of mixed-to-greasy skin, and it is then possible to add thereto a specific active agent for the treatment of greasy skin, such as, for example, salicylic acid derivatives, for instance n-octanoyl-salicylic acid, copper gluconate, niacinamide (vitamin PP) and mixtures thereof.

Another subject of the invention is a cosmetic process for the treatment of combination and greasy skin, comprising applying, to the skin, a composition as defined above, and in rinsing the skin.

The compositions according to the invention can be used in at least two ways:

the first use includes spreading the composition (e.g., gel) in the hands, in applying it to the face or to the body, and then in massaging it in the presence of water so as to develop the foam directly on the face or the body;

another possible use of this type of product includes developing the foam in the palms of the hands before applying it to the face or the body.

In the two cases, the foam is then preferably rinsed off with water or wiped off with a towelette, a glove or cotton wool, etc.

The composition can also be used dry on the areas to be treated, and then rinsed off with water.

The examples which follow serve to illustrate the invention without, however, being limiting in nature.

The amounts indicated are in % by weight unless otherwise mentioned.

In the tables below, all the percentages are expressed by weight of starting material (S.M.), the amount of active material (A.M.) being specified between parentheses.

Examples 1 to 4

According to the Invention

| Composition (% SM) | Ex. 1 | Ex. 2 | Ex. 3 | Ex. 4 |
|---|---|---|---|---|
| $C_{12}$-$C_{16}$ Alkyl polyglucoside (1) | 17.16 (A.M. 8.58%) | 17.16 (A.M. 8.58%) | 17.16 (A.M. 8.58%) | 17.16 (A.M. 8.58%) |
| Lauryldimethyl betaine (2) | 13 (A.M. 3.9%) | 13 (A.M. 3.9%) | 13 (A.M. 3.9%) | 13 (A.M. 3.9%) |
| Crosslinked sodium polyacrylate (3) | 2 | | | |
| Starch modified with crosslinked acrylamide/sodium acrylate (4) | | 2 | | |
| Starch/guar gum/sodium carboxymethylcellulose (5) | | | 4 | |
| Starch modified with crosslinked acrylamide/sodium acrylate (6) | | | | 2 |
| Dimethyldiallylammonium/acrylamide copolymer (7) | | | | 2.87 (A.M. 0.249%) |
| Citric acid | qs pH 7 | qs pH 7 | qs pH 7 | qs pH 7 |
| Water | qs 100% | qs 100% | qs 100% | qs 100% |
| Appearance | Translucent | Translucent, frosty | Translucent | Translucent |
| Viscosity at 20° C. (rheometer Rheo RS150 0.1 s$^{-1}$) | 40 Pa · s | 270 Pa · s | 500 Pa · s | 300 Pa · s |

(1) Plantacare 818 UP at 50% of A.M.
(2) Empigen BB/LS at 30% of A.M.
(3) Luquasorb 1010 (BASF)
(4) Waterlock C200 (Grain Processing)
(5) Lysorb 220 (Lysorb)
(6) Waterlock A100 (Grain Processing)
(7) Merquat S (Nalco) or polyquaternium-7 at 8.7% of A.M.

Procedure:

The mixture of surfactants was heated to 50° C. and then the superabsorbent polymer was introduced therein. The mixture was allowed to swell for 30 minutes and the pH was adjusted with citric acid.

Comparative Examples 5 and 6

| Composition (% S.M.) | Comparative Example 5 | Comparative Example 6 |
|---|---|---|
| $C_{12}$-$C_{16}$ Alkyl polyglucoside (1) | 17.16 (A.M. 8.58%) | 17.16 (A.M. 8.58%) |
| Lauryldimethyl betaine (2) | 13 (A.M. 3.9%) | 13 (A.M. 3.9%) |
| Carbomer (8) | 2 | — |
| Maize starch modified with hydroxypropyl phosphate (9) | — | 2 |
| Citric acid | qs pH 7 | qs pH 7 |
| Water | qs 100% | qs 100% |
| Appearance | Fluid opaque gel | Translucent solution which undergoes phase separation in 24 hours |
| Viscosity at 20° C. (rheometer Rheo RS150 0.1 s$^{-1}$) | 72 Pa · s | Not measurable |

(1) Plantacare 818 UP at 50% of A.M.
(2) Empigen BB/LS at 30% of A.M.
(8) Carbopol 981
(9) Structure XL Sensory Performance Levels:

The sensory performance levels of the compositions (foam qualities) were determined according to the protocol described below.

Before any use of the product, the hands are washed with household soap and then suitably rinsed and dried. Next, the protocol followed is the following:

1—the hands are wetted by passing them under running water, and shaking them three times to dry them, 2—1 g of product is placed in the hollow of one of the hands, 3—the product is worked between the two palms for 10 seconds, 4—2 ml of water are added and the product is again worked for 10 seconds, 5—2 ml of water are added and the product is again worked for 10 seconds, 6—the quality of the foam is evaluated according to the criteria defined below, 7—the hands are rinsed under water, 8—they are wiped.

The foam criteria are marked on a scale of 0 to 10.

Step 2: evaluation of the mixture with water,

Steps 4-6: evaluation of the foam quality,

Homogeneity of the composition shared between the hands: the mark attributed is higher the better the homogeneity, The start of lathering: the mark attributed is higher the better the starting of lathering, The volume of foam: the mark attributed is higher the greater the volume, The density of the foam: the mark attributed is higher the greater the density.

The evaluation panel consists of 5 trained experts. The average of the 5 marks makes it possible to compare the compositions according to each of the criteria.

|  | Ex. 1 | Ex. 2 | Ex. 3 | Ex. 4 | Comparative Ex. 5 |
|---|---|---|---|---|---|
| Polymer | Luquasorb 1010 | Waterlock C200 | Lysorb 220 | Waterlock A100 | Carbopol 981 |
| Homogeneity | 10/10 | 10/10 | 10/10 | 10/10 | 7/10 |
| Starting of lathering | 5/10 | 5/10 | 5/10 | 7/10 | 0/10 |
| Foam volume | 6.5/10 | 7/10 | 6/10 | 10/10 | 2.3/10 |
| Foam density | 7.5/10 | 8/10 | 6.5/10 | 8.5/10 | 2/10 |
| Bubble size | 3.5/10 | 3/10 | 3/10 | 4.5/10 | 3.2/10 |
| Result | + | + | + | + | − |

The gel of Comparative Example 5, based on carbopol, produces less homogeneous foams for which the starting of lathering is not good and the volume is very small and the density is low.

Example 7

According to the Invention

| Composition (% SM) | Example 7 according to the invention |
|---|---|
| $C_{12}$-$C_{16}$ Alkylpolyglucoside (1) | 24.53% |
| Crosslinked sodium polyacrylate (2) | 2% |
| Polyaminopropyl biguanide (3) | 0.5% |
| Citric acid | qs pH 6.5 |
| Water | qs 100% |
| Stability after 2 months at all temperatures | stable |

(1) Plantacare 818 UP 50% AM
(2) Luquasorb 1010 (BASF)
(3) Cosmocil CQ 20% AM

The above written description of the invention provides a manner and process of making and using it such that any person skilled in this art is enabled to make and use the same, this enablement being provided in particular for the subject matter of the appended claims, which make up a part of the original description and including a cleansing composition for topical application, in the form of a gel and containing, in a physiologically acceptable aqueous medium, at least 35% by weight of water relative to the total weight of the composition, at least one foaming surfactant chosen from nonionic surfactants and amphoteric surfactants, and at least one superabsorbent polymer.

As used herein, the phrases "selected from the group consisting of," "chosen from," and the like include mixtures of the specified materials. Terms such as "contain(s)" and the like as used herein are open terms meaning 'including at least' unless otherwise specifically noted. Phrases such as "mention may be made," etc. preface examples of materials that can be used and do not limit the invention to the specific materials, etc., listed.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of a gel comprising, relative to the total weight of the composition,
    at least 35% by weight of water,
    from 3 to 20% by weight an alkyl polyglucoside foaming surfactant having an HLB value of greater than 15 and optionally a betaine derivative having an HLB value of greater than 15;
    from 0.1 to 20% by weight of at least one superabsorbent polymer; and
    an anionic surfactant in an amount of 2% by weight or less.

2. The composition according to claim 1, wherein the at least one superabsorbent polymer is chosen from cross-linked sodium polyacrylates, starches grafted with an acrylic polymer, hydrolysed starches grafted with an acrylic polymer, polymers based on starch, on gum and on a cellulose derivative, and mixtures thereof.

3. The composition according to claim 1, comprising at least one nonionic surfactant and at least one amphoteric surfactant.

4. The composition according to claim 1, further comprising at least one cationic polymer.

5. The composition according to claim 4, wherein the cationic polymer is chosen from polyquaternium 5, polyquaternium 7, polyquaternium 28, polyquaternium 39, polyquaternium 44, polyquaternium 47, and mixtures thereof.

6. The composition according to claim 4, wherein the amount of cationic polymer(s) ranges from 0.1% to 1% by weight, relative to the total weight of the composition.

7. The composition according to claim 1, wherein said composition is free of an anionic surfactant.

8. The composition according to claim 1, wherein said composition is a cleansing and/or makeup-removing product for the skin, the scalp and/or the hair, and/or a scrubbing product or an exfoliant product for the skin.

9. A method for cleansing and/or removing makeup from the skin and/or the hair, and/or for scrubbing the skin, comprising applying the composition of claim 1 to the skin and/or the hair.

10. The method according to claim 9, comprising applying the composition to greasy skin, and rinsing the skin.

11. The method according to claim 9, comprising spreading the composition in a users hands and then applying it to the face, body, and/or hair, and then massaging the composition in the presence of water so as to develop a foam.

12. The method according to claim 9, comprising developing a foam from said composition and water in the palms of a users hands followed by applying the foam to the face, body or hair.

13. The composition according to claim 1, comprising a betaine derivative having an HLB value of greater than 15.

* * * * *